United States Patent [19]

Lau

[11] Patent Number: 5,383,860
[45] Date of Patent: Jan. 24, 1995

[54] TWO-PART CONDUCTIVE CANNULA WITH ADAPTIVE DISPOSABLE NON-INVASIVE ELEMENT

[75] Inventor: Michael Lau, Edmonds, Wash.

[73] Assignee: M.I.S. Technology International, Inc., Singapore

[21] Appl. No.: 25,024

[22] Filed: Mar. 2, 1993

[51] Int. Cl.⁶ ............................................. A61M 5/178
[52] U.S. Cl. .................................... 604/167; 604/164; 604/169; 604/256
[58] Field of Search ............... 604/164, 167, 169, 256, 604/280, 283

[56] References Cited

U.S. PATENT DOCUMENTS

| | | |
|---|---|---|
| 4,436,519 | 3/1984 | O'Neill . |
| 4,626,245 | 12/1986 | Weinstein ............................ 604/256 |
| 4,649,904 | 3/1987 | Krauter et al. ..................... 604/167 |
| 4,655,752 | 4/1987 | Honkanen et al. . |
| 4,946,133 | 8/1990 | Johnson et al. ..................... 604/256 |
| 5,009,643 | 4/1991 | Reich et al. ......................... 604/167 |
| 5,104,383 | 3/1992 | Shichman ............................ 604/167 |
| 5,122,122 | 6/1992 | Allgood . |
| 5,176,651 | 1/1993 | Allgood et al. ..................... 604/167 |
| 5,211,633 | 5/1993 | Stouder, Jr. ......................... 604/167 |
| 5,224,930 | 7/1993 | Spaeth ................................. 604/169 |
| 5,242,412 | 9/1993 | Blake, III ............................ 604/167 |

Primary Examiner—C. Fred Rosenbaum
Assistant Examiner—Perry E. Van Over
Attorney, Agent, or Firm—Seed and Berry

[57] ABSTRACT

A two-part cannula is described comprising an invasive portion of a conductive material and a non-invasive portion adapted for coupling to any one of a number of invasive portions. The invasive portions can have differing characteristics such as lengths and internal diameters. The inventive device permits a variety of surgical instruments having differing diameters to be used in conjunction with closely conforming invasive portions without requiring a variety of non-invasive portions.

7 Claims, 1 Drawing Sheet

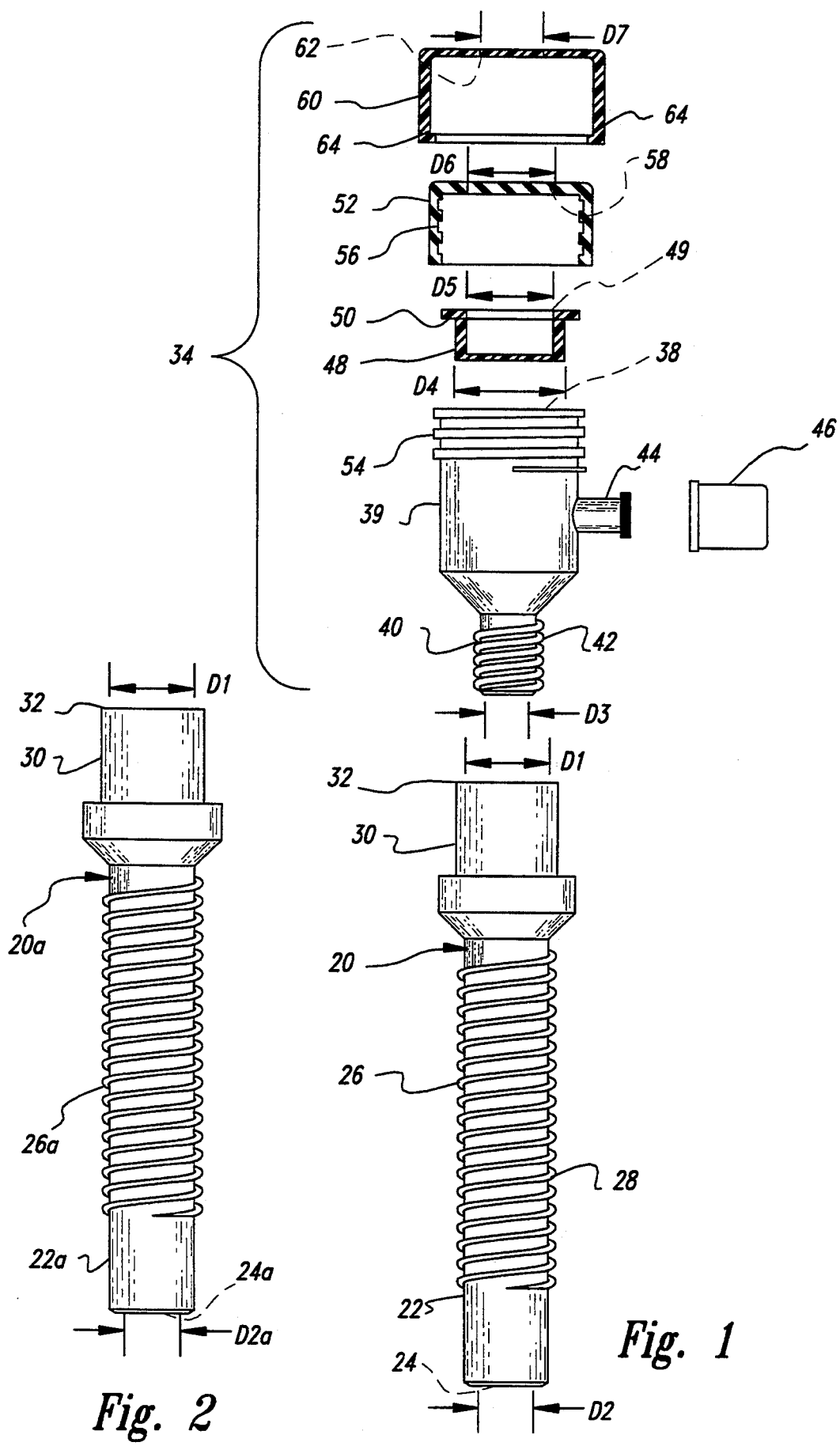

TWO-PART CONDUCTIVE CANNULA WITH ADAPTIVE DISPOSABLE NON-INVASIVE ELEMENT

TECHNICAL FIELD

The present invention relates to a two-part surgical cannula incorporating a conductive invasive portion and a plastic, disposable non-invasive portion.

BACKGROUND OF THE INVENTION

In recent years, minimally invasive surgery has been gaining increased popularity. This type of surgery, utilizing an endoscope through minor skin incisions, has multiple applications in gynecology, general surgery, thoracic surgery, urology and orthopedics.

The trocar/cannula provides the portal for inducing instruments into the body cavities of interest. In the case of laparoscopy, the trocar/cannula provides the portal into the peritoneal cavity.

Traditionally, trocar and cannula are reusable and are made of metal. The cannula consists of a sleeve, the channel through which the instruments can pass. In order to insufflate the abdominal cavity with carbon dioxide, a side port usually is placed near the top of the cannula for the intake of gas. For the abdominal cavity to remain inflated while an instrument is not in the cannula, a valve in a non-invasive portion of the cannula prevents gas from escaping through the cannula. The valve usually uses a trumpet or trapdoor mechanism.

Typically, trocar and cannula are reusable. However, after use, blood and other body fluids contaminate the cannula parts. With the increasing awareness of risks of transmission of diseases, such as HIV virus and hepatitis, through blood and other body fluids, cleaning and sterilizing the trocar and cannula are of great concern.

Common cannula present the difficulty in cleaning and sterilizing after each use. In particular, side port and valve mechanisms, which usually include springs and mechanical parts, are hard to disassemble and clean.

Though the most difficult part of a cannula to clean and sterilize is the non-invasive portion containing the small side port for gas and the gas retention valve with all its mechanical parts, the cannula sleeve itself is usually only a hollow tube that can be easily cleaned and sterilized.

To address this problem of cleaning and sterilization, a disposable cannula/trocar was introduced a few years ago. These disposable instruments are usually made of plastic and are single-use devices. While reducing the problem of contamination and cleaning costs, these devices introduce two additional problems. First, because the plastic cannula sleeve is electrically nonconductive, its electrical properties can cause electrosurgical damage as described below. Moreover, the disposable plastic cannula/trocar impose a high-cost per use.

The problem of electrosurgical damage is known in the art. Essentially, where a monopolar electrode is used, especially through a metal laparoscope in the cannula, capacitive coupling potentially can lead to arcing between the laparoscope and any nearby organs. This occurs primarily in nonconductive sleeves because they are unable to dissipate the electrical energy through the abdominal or similar wall as a metal cannula sleeve can. Even where an electrode is not inserted through the cannula, charge coupling within the body may occur due to the touching of an active electrode to a laparoscope with a plastic cannula. This can result in electrical discharge to nearby organs. In abdominal surgery, this occurs most frequently in the bowel.

The lower risk associated with reduced contamination risk is thus offset by a higher risk of electrosurgical damage. One attempt to reduce the problem of contamination while retaining conductivity employs a two-part metal cannula. While improving the cleaning process, the non-invasive portion is reused raising the risk of contamination. Further, the non-invasive portion does not lend itself to easy manufacture. Moreover, there is no provision for using varying caliber invasive portions with a single non-invasive portion or structure.

SUMMARY OF THE INVENTION

The inventive device addresses the problems of the prior art by providing a cannula with two portions having differing characteristics and by employing a coupling adapting any non-invasive portion to a series of invasive portions. The non-invasive portion is designed to remain outside the body during use. The non-invasive portion contains a gas side port, a trocar valve and a cap that fits snugly around the instrument inserted through the cannula. The gas side port allows insufflation of the abdomen during use and the diaphragm valve prevents the escape of gas from the abdomen when no instrument is inserted through the cannula. The snug fitting cap helps to retain inserted instruments in a relatively central position as they pass through the cannula.

The non-invasive portion of the cannula, consisting of the aforementioned parts, functions as a unit and it is disposable, thus avoiding the problem of cleaning and sterilization after each use. The non-invasive portion of the cannula also comprises a uniform coupler for mechanical attachment to an invasive portion.

The invasive portion comprises a hollow, conductive sleeve. Cleaning and sterilization of the hollow cannula sleeve is easily accomplished using the usual operating room procedures.

The uniform coupler allows identical non-invasive portions to be used with invasive portions having differing characteristics. For example, varying diameter, length, external surface configuration, and electrical conductivity may be desirable, depending on the operative requirement. In particular, differing diameters of invasive portions can be tailored to the caliber of the inserted instrument, and the various lengths of invasive portions can be tailored to the thickness of the abdominal wall associated with various body builds.

Threads are included in the external surface of the invasive portion of the preferred embodiment to increase its retention in tissue layers, especially the fascia layers, to prevent unintentional sliding of the cannula in or out of the abdominal wall. The invasive portion is constructed of electrically conductive material such as metal to improve the electrical safety of the laparoscopic instrument application.

It is an advantage of the inventive device that the invasive portion can be easily cleaned and sterilized and reused to save cost. On the other hand, the disposable top portion of the cannula which contains the most difficult parts to clean and sterilize, can be discarded after each case, thus saving the labor-intensive cleaning and sterilization cost. The uniform coupler allows identical fabrication of a single non-invasive portion structure able to mate with different invasive portion configurations and thus furthers the cost savings.

It is an object of the invention to describe a cannula that is electrically safe and easy to clean and sterilize to avoid risk of cross-contamination. It is a further object of the invention to provide a cannula that incorporates an interchangeability of invasive portions with a single configuration of the non-invasive portion, while preserving the electrical safeguards of the invasive portion.

BRIEF DESCRIPTION OF THE DRAWINGS

FIG. 1 is an exploded view of the preferred embodiment of the device.

FIG. 2 is an alternative embodiment of a portion of the device shown in FIG. 1.

DETAILED DESCRIPTION OF THE INVENTION

In FIG. 1, an invasive portion 20 comprises a cylindrical section 22 having a central passageway 24. An invasive portion retainer 26 is located on an outer surface 28 of the invasive portion. The invasive portion retainer functions to retain the invasive portion within the patient during surgery. In the preferred embodiment, the invasive portion retainer comprises threads helically surrounding the outer surface. Other invasive portion retainers will be obvious to those skilled in the art.

The invasive portion 20 further comprises an invasive portion coupler 30 at its axially outer end 32. In the preferred embodiment of the device, the invasive portion coupler 30 comprises a threaded receptacle having an internal diameter D1.

The central passageway 24 passes through the entire cylindrical section with an internal diameter D2 adapted to closely accommodate a trocar of a known diameter. While the preferred embodiment of the device incorporates a fixed diameter D2 in the central passageway, it will be obvious to one skilled in the art to use a nonconstant diameter.

It is an advantage of this device that the invasive portion 20 is a non-complex structure which may be constructed easily of a conductive material, such as a metal, to prevent electrosurgical injury.

A non-invasive portion 34 adaptively couples to the invasive portion 20 at the coupler 30 by matching threads. The non-invasive portion has a cylindrical main section 39 of an internal diameter D4, larger than the diameter D2 of the central passageway 24. The non-invasive portion 34 tapers to a narrow section 40, where threads 42 are located. The narrow section has an internal diameter D3 larger than or equal to the internal diameter D2 of the central passageway and an external threaded diameter which firmly threadably engages into the threads of the internal diameter D1 of coupler 30.

A side port 44 with a valve cap 46 is positioned on the cylindrical main section 39. The side port permits coupling of a line to permit insufflation of the subject during an operation. A gas retention valve is seated in the side port to limit the flow of gases through the side port. Such gas retention valves and side ports are known in the art. The valve cap provides additional protection to prevent escape of gases.

A trocar valve 48 having an upper lip 50 with an opening 49 of an inner diameter D5 is seated in the main section 39. The trocar valve diameter D5 is chosen to be larger than or equal to the diameter D2 of the invasive portion 20. A top cap 52 mounts to the main section and is held in place by complementary threads 54, 56. When in place, the top cap holds the trocar valve in place. The trocar valve is a known valve of a flexible material, typically latex. The central portion of such a latex trocar valve typically contains a semirigid latex layer with 1 to 4 radial cuts which section the central portion. The sections flex to allow the trocar to pass through while sealing around the trocar.

While the trocar valve 48 is shown as being held by the top cap 52, the trocar valve may be located at any point along the device such as in the narrow section 40. Such relocation of the trocar valve will be obvious to one skilled in the art. A top cap aperture 58 having a diameter D6 allows access through the top cap.

A top cap cover 60 of a flexible material, such as latex, with a lower lip 64 covers the top cap 52. The top cap cover has a cover aperture 62 having a diameter D7. The cover aperture diameter D7 is smaller than the diameter D6 of top cap aperture 58 and is smaller than the internal diameter D2. This permits the top cap cover to flexibly engage a trocar passing through the top cap.

Operation and assembly of the inventive device will now be described. The inventive device is first assembled with the top cap 52 threaded over the main section 39 such that the trocar valve 48 is held firmly in place between them. The top cap cover 60 is stretched over the top cap where it is held in place by the lower lip 64. The valve cap 46 is placed over the side port 44.

The narrow section 40 of the fully-assembled non-invasive portion 34 is then threaded into the coupler 30 of the invasive portion 20 to form a single unit. An 0-ring or gasket may be placed in the invasive portion coupler prior to assembly to reduce leakage.

The single unit can then be inserted into a patient, typically through the wall of the abdomen, with a portion of the cylindrical section 22 of the invasive portion 20 actually penetrating the patient. The invasive portion retainer 26 prevents the invasive portion from sliding easily out of the patient, by providing an interface between the cylindrical section and the abdominal wall or similar tissue.

Control of the gas content and pressure level within the patient can be achieved by supplying gas to the side port 44. This is realized by removing the valve cap 46 and coupling a gas line to the side port in a manner known in the art, such as by a flexible latex tip or a spring-loaded clamp.

Prior to inserting the unit into a patient, a typical trocar having a cylindrical outer surface and a sharp distal end is inserted through the cover aperture 62. Such a trocar is well known in the art. The trocar passes through a path comprising the top cap 52, the trocar valve 48, the main section 39, the narrow section 40, the invasive portion coupler 30 and the cylindrical section 22. The sharp distal end of the trocar extends out of the unit, providing a sharp edge to permit penetration of the patient's tissue. After the trocar and the invasive portion enter the patient and a passageway is created, the trocar is removed and surgical instruments may be inserted through the unit along the same path as the trocar.

Gases from within the patient are prevented from escaping from around the trocar by the trocar valve 48 and the cover aperture 62, which form seals around the trocar by flexibly engaging it circumferentially. When the trocar is removed, gases from within the patient are prevented from escaping through the unit by the trocar valve, which returns to its undeformed position to form a seal.

The cover aperture 62, the top cap aperture 58, the trocar valve opening 49, the main section 39 and the narrow section 40 are formed with internal diameters greater than or equal to the diameter D2 of the central passageway 24. The non-invasive portion diameters need not conform closely to the trocar or surgical instrument diameter due to the use of flexible materials for the top cap cover 60 and the trocar valve 48 to expandably retain and seal the surgical instrument within the non-invasive portion 34. This permits the invasive portion 20 to have a uniform internal threaded coupling diameter D1 regardless of the diameter D2 of the central passageway. This allows the non-invasive portion to be used with a variety of different invasive portions 20 having differing diameters.

It is an advantage of this device that the non-invasive portion 34 is designed to couple to invasive portions 20 having a range of diameters D2. This advantage is more readily apparent when a second invasive portion 20a is considered as shown in FIG. 2. The second invasive portion 20a is shown with an identical threaded coupler 30 having a threaded internal diameter D1. The second invasive portion has a central passageway 24a, a different internal diameter D2a, and a cylindrical section 22a having a different length from the cylindrical section 22 of the invasive portion.

The second invasive portion 20a couples to the non-invasive portion 34 interchangeably with the first invasive portion. Because each of the invasive portion 20 and the second invasive portion 20a has a uniform coupler 30, either can be used with the non-invasive portion 34. The invasive portions 20, 20a can then be chosen independently of the non-invasive portion to permit use of invasive portions matched to surgical instruments of varying diameters with a uniform non-invasive portion. For example, the invasive portion 20 may have a central passageway diameter D2 of 12 mm, allowing insertion of and conformance to instruments of approximately 12 mm, while the second invasive portion 20a may have a central passageway diameter D2a of 15 mm, allowing insertion of and conformance to larger diameter instruments.

It is an advantage of the device that the top cap 60, the main section 39, the narrow section 40, the side port 44, and the threads thereon are made of plastic or other moldable material. This permits the non-invasive portion to be formed substantially by injection molding reducing the costs to the extent that the non-invasive portions are readily disposable. Because any disposable non-invasive portions 34 can be used with either of the invasive portions 20, 20a, disposal of the invasive portions is not required.

I claim:

1. A cannula system including a non-invasive portion and a plurality of alternatively, interchangeable invasive portions comprising:

a disposable non-invasive portion of a first material comprising molded plastic, the non-invasive portion having an axially inner end, an axially outer end, a passageway extending therethrough from the axially inner end to the axially outer end, and a portion including a non-invasive portion coupling element adjacent the inner end for alternatively and interchangeably engaging and connecting to invasive portions;

a first invasive portion of a second material comprising an electrically conductive material and having an axially outer end, a coupling element for removably connecting the first invasive portion with the coupling element of the non-invasive portion at said axially outer end, an axially inner end and an invasive portion passageway extending from the invasive portion axially outer end to the invasive portion axially inner end and alignable with the passageway in the non-invasive portion when the non-invasive and first invasive portions are coupled, the invasive portion passageway of the first invasive portion being defined by a conductive inner surface such that the first invasive portion provides an electrically conductive pathway for dissipation of charge from a surgical instrument inserted in the invasive portion passageway and engaging the inner surface to the tissue invaded by and engaged by an outer conductive surface of the first invasive portion when in use; and a second invasive portion of an electrically conductive material and having an axially outer end, a coupling element for removably connecting the second invasive portion with the coupling element of the non-invasive portion at said axially outer end, an axially inner end, and an invasive portion passageway extending from the second invasive portion axially outer end to the second invasive portion axially inner end and alignable with the passageway in the non-invasive portion when the non-invasive and second invasive portions are coupled, the invasive portion passageway of the second invasive portion being defined by a conductive inner surface such that the second invasive portion provides an electrically conductive pathway for dissipation of charge from a surgical instrument inserted in the invasive portion passageway and engaging the inner surface to the tissue invaded by and engaged by an outer conductive surface of the second invasive portion when in use; and each of the first coupling element and the second coupling element being adapted for rigid coupling to the non-invasive portion coupling element of said non-invasive portion wherein the first invasive portion has a threaded exterior providing retention when the first invasive portion is inserted into a patient, the threaded exterior being directed such that the first invasive portion is urged toward a more invasive position as the non-invasive portion is detached from the invasive portion.

2. A cannula system including a non-invasive portion and a plurality of alternatively, interchangeable invasive portions comprising:

a disposable non-invasive portion of a first material comprising molded plastic, the non-invasive portion having an axially inner end, an axially outer end, a passageway extending therethrough from the axially inner end to the axially outer end, and a portion including a non-invasive portion coupling element adjacent the inner end for alternatively and interchangeably engaging and connecting to invasive portions;

a first invasive portion of a second material comprising an electrically conductive material and having an axially outer end, a first coupling element for removably connecting the first invasive portion with the coupling element of the non-invasive portion at said axially outer end, an axially inner end and an invasive portion passageway having a first invasive portion diameter extending from the invasive portion axially outer end to the invasive portion axially inner end and alignable with the passageway in the non-invasive portion when the non-invasive and first invasive portions are coupled, the invasive portion passageway of the first invasive portion being defined by a conductive inner surface such that the first invasive portion provides an electrically conductive pathway for dissipation of charge from a surgical instrument inserted in the invasive portion passageway and engaging the inner surface to the tissue invaded by and engaged by an outer conductive surface of the first invasive portion when in use; and a second invasive portion of an electrically conductive material and having an axially outer end, a second coupling element for removably connecting the first invasive portion with the coupling element of the non-invasive portion at said axially outer end, an axially inner end, and an invasive portion passageway having a second invasive portion diameter extending from the second invasive portion axially outer end to the second invasive portion axially inner end and alignable with the passageway in the non-invasive portion when the non-invasive and second invasive portions are coupled, the invasive portion passageway of the first invasive portion being defined by a conductive inner surface such that the second invasive portion provides an electrically conductive pathway for dissipation of charge from a surgical instrument inserted in the invasive portion passageway and engaging the inner surface to the tissue invaded by and engaged by the outer conductive surface of the second invasive portion when in use; and each of the first coupling element and the second coupling element adapted for rigid coupling to the non-invasive portion coupling element of said non-invasive portion wherein the non-invasive portion further includes a molded plastic top cap having a top cap aperture therethrough and a top cap cover located at the axially outer end of said non-invasive portion the top cap cover having a top cap cover aperture therethrough, the top cap aperture and top cap cover aperture being axially aligned with the passageway of the non-invasive portion and a trocar valve, said trocar valve being located in the non-invasive portion passageway, the top cap cover and trocar valve being sufficiently flexible to accommodate inserted tools having diameters varying from substantially equal to the first invasive portion diameter to the second invasive portion diameter.

3. The cannula system of claim 2 wherein the non-invasive portion coupling element is an externally threaded narrow section.

4. A cannula system including a non-invasive portion and a plurality of alternatively, interchangeable invasive portions comprising:

a disposable non-invasive portion of a first material comprising molded plastic, the non-invasive portion having an axially inner end, an axially outer end, a passageway extending therethrough from the axially inner end to the axially outer end, and a portion including a non-invasive portion coupling element adjacent the inner end for alternatively and interchangeably engaging and connecting to invasive portions;

a first invasive portion of a second material comprising an electrically conductive material having an axially outer end, a coupling element for removably connecting the first invasive portion with the coupling element of the non-invasive portion at said axially outer end, an axially inner end and an invasive portion passageway having a first invasive portion internal diameter extending from the invasive portion axially outer end to the invasive portion axially inner end and alignable with the passageway in the non-invasive portion when the non-invasive and first invasive portions are coupled, the invasive portion passageway of the first invasive portion being defined by a conductive inner surface such that the first invasive portion provides an electrically conductive pathway for dissipation of charge from a surgical instrument inserted in the invasive portion passageway and engaging the inner surface to the tissue invaded by and engaged by the outer conductive surface of the first invasive portion when in use; and a second invasive portion of an electrically conductive material and having an axially outer end, a coupling element for removably connecting the first invasive portion with the coupling element of the non-invasive portion at said axially outer end, an axially inner end, and an invasive portion passageway having a second invasive portion internal diameter extending from the second invasive portion axially outer end to the second invasive portion axially inner end and alignable with the passageway in the non-invasive portion when the non-invasive and second invasive portions are coupled, the invasive portion passageway of the first invasive portion being defined by a conductive inner surface such that the second invasive portion provides an electrically conductive pathway for dissipation of charge from a surgical instrument inserted in the invasive portion passageway and engaging the inner surface to the tissue invaded by and engaged by the outer conductive surface of the second invasive portion when in use; and each of the first coupling element and the second coupling adapted for rigid coupling to the non-invasive portion coupling element of said non-invasive portion wherein invasive portion has a first internal diameter and the second invasive portion has a second internal diameter, and the second internal diameter is greater than the first internal diameter and the coupling elements include rotatably mating portions thereof so that the coupling elements are mateable by rotation with respect to each other.

5. The cannula system of claim 4 wherein the internal diameter of the first invasive portion is approximately 12 mm and the second invasive portion internal diameter is approximately 15 mm.

6. A cannula system including a disposable non-invasive portion for use with surgical instruments with external diameters ranging from a first diameter to a second diameter, the non-invasive portion comprising:

a top cap having a first internal diameter;

a substantially cylindrical narrow section axially alignable with the top cap and having a second internal diameter the narrow section being adapted for rigid coupling to an invasive portion;

a main section having a third internal diameter the main section being positioned intermediate the top cap and the narrow section and being axially aligned therewith to provide a passageway through the non-invasive portion, the narrow section and the main section being a unitary piece;

a trocar valve within the passageway operatively sized to accommodate each of said surgical instruments of differing diameters the trocar valve inhibiting the escape of fluids through the passageway;

a top cap cover mateable to the top cap and having a top cap aperture therethrough, the top cap aperture being axially aligned with the passageway when the top cap cover is mated to the top cap, the top cap cover further being operatively sized and of sufficient flexibility to permit passage of each such surgical instrument while radially engaging each such surgical instrument, the first internal diameter, the second internal diameter and the third internal diameter each being larger than either of the first diameter and the second diameter of said surgical instruments;

the top cap, the main section, and the narrow section being formed of molded plastic; and a plurality of conductive invasive portions each comprising an internal passageway with an internal passageway diameter closely conforming to a surgical instrument of a respective predetermined diameter and a coupler adapted for rigid coupling to the narrow section wherein the an internal passageway diameter of a first one of the invasive portions is greater than an internal passageway diameter of a second one of the invasive portions.

7. The cannula system of claim 6 wherein the internal passageway diameter of a first of the invasive portions is approximately 12 mm and the internal passageway diameter of a second of the invasive portions is approximately 15 mm.

* * * * *

UNITED STATES PATENT AND TRADEMARK OFFICE
CERTIFICATE OF CORRECTION

PATENT NO. : 5,383,860
DATED : January 24, 1995
INVENTOR(S) : Michael Lau

It is certified that error appears in the above-identified patent and that said Letters Patent is hereby corrected as shown below:

In column 6, claim 1, line 3, following the word "a" please insert --first--.

In column 6, claim 1, line 22, following the word "a" please insert --second--.

In column 7, claim 2, line 19, please delete "first" and insert therefor --second--.

In column 8, claim 4, line 5, following the word "a" please insert --first--.

In column 8, claim 4, line 25, following the word "a" please insert --second--.

In column 8, claim 4, line 27, please delete "first" and insert therefor --second--.

In column 8, claim 4, line 48, following "wherein" please insert --the first--.

Signed and Sealed this

Tenth Day of November 1998

*Attest:*

BRUCE LEHMAN

*Attesting Officer*  *Commissioner of Patents and Trademarks*